United States Patent [19]
El A'mma et al.

[11] Patent Number: 6,008,238
[45] Date of Patent: Dec. 28, 1999

[54] STABILIZATION OF 3-ISOTHIAZOLONE SOLUTIONS

[75] Inventors: Beverly Jean El A'mma, Perkiomenville; John Robert Mattox, Perkasie, both of Pa.

[73] Assignee: Rohm and Haas Company, West Phila, Pa.

[21] Appl. No.: 09/023,938

[22] Filed: Feb. 13, 1998

Related U.S. Application Data

[60] Provisional application No. 60/063,349, Oct. 28, 1997.

[51] Int. Cl.⁶ .......................... A01N 43/80; A01N 59/20; A01N 55/02; A01N 25/22
[52] U.S. Cl. .......................... 514/372; 514/373; 514/499; 514/500; 514/970; 514/971; 514/973; 424/630; 424/632; 424/633; 424/634; 424/635; 424/637; 424/638; 424/661; 424/662; 424/667; 424/668; 504/151; 504/156
[58] Field of Search .................................... 514/372, 373, 514/970, 971, 973, 499, 500; 504/151, 156; 424/630, 632–635, 637–638, 661–662, 667–668

[56] References Cited

U.S. PATENT DOCUMENTS

| | | | |
|---|---|---|---|
| 3,870,795 | 3/1975 | Miller et al. | 514/372 |
| 5,153,213 | 10/1992 | Schmidt | 514/372 |
| 5,461,150 | 10/1995 | Gironda et al. | 548/213 |
| 5,869,510 | 2/1999 | Mattox | 514/372 |
| 5,910,503 | 6/1999 | Mattox et al. | 514/372 |
| 5,922,745 | 7/1999 | McCarthy et al. | 514/372 |

FOREIGN PATENT DOCUMENTS

| | | |
|---|---|---|
| 0542 408 A1 | 8/1992 | European Pat. Off. . |
| 0 606 986 A1 | 1/1994 | European Pat. Off. . |
| 0749689A2 | 5/1996 | European Pat. Off. . |
| 0773282 A1 | 10/1996 | European Pat. Off. . |

*Primary Examiner*—John Pak
*Attorney, Agent, or Firm*—S. Mathew Cairns

[57] ABSTRACT

Disclosed is a stable dilute solution composition of a 3-isothiazolone compound selected from the group consisting of 5-chloro-2-methyl-3-isothiazolone, 2-methyl-3-isothiazolone, 5-chloro-2-ethyl-3-isothiazolone, 2-ethyl-3-isothiazolone, 4,5-dichloro-2-methyl-3-isothiazolone, and mixtures thereof in water having extremely low levels of copper ion and an oxidant.

10 Claims, No Drawings

STABILIZATION OF 3-ISOTHIAZOLONE SOLUTIONS

This application claims benefit of provisional application 60/063,349, filed on Oct. 28, 1997.

BACKGROUND OF THE INVENTION

This invention relates to stabilization of 3-isothiazolones microbicides. In particular, this invention relates to the stabilization of dilute solutions of 3-isothiazolone microbicides having very low levels of copper ion.

Microbicides are used commercially to prevent the growth of microbes in a variety of loci, such as cooling towers, metal working fluid systems, paint and cosmetics. One of the more important classes of microbicides is 3-isothiazolones. Many 3-isothiazolones have achieved commercial success because they are very effective in preventing microbial growth under a wide variety of conditions and in a variety of loci. Among the most important 3-isothiazolones are 5-chloro-2-methyl-3-isothiazolone, 2-methyl-3-isothiazolone, and mixtures thereof.

Although 3-isothiazolones are highly effective microbicides, some 3-isothiazolones suffer from being unstable under certain conditions. Without the presence of a stabilizer, many 3-isothiazolones chemically degrade and lose microbicidal efficacy. Much research has been devoted to stabilizing 3-isothiazolones.

Typical 3-isothiazolone products of a 3:1 mixture of 5-chloro-2-methyl-3-isothiazolone and 2-methyl-3-isothiazolone contain between 1 and 25 percent by weight of the 3-isothiazolone mixture and a similar amount of a stabilizer. Concentrate compositions of a 3:1 mixture of 5-chloro-2-methyl-3-isothiazolone and 2-methyl-3-isothiazolone generally contain about 5 to 35 percent by weight of the 3-isothiazolone compounds and require about 10 to 25 percent by weight of a stabilizer. Dilute solutions of a 3:1 mixture of 5-chloro-2-methyl-3-isothiazolone and 2-methyl-3-isothiazolone contain about 0.5 to 5 percent by weight of the 3-isothiazolone compounds. Dilute solutions have different stabilization requirements from 3-isothiazolone concentrates.

A variety of stabilizers for 3-isothiazolone dilute solutions are known. These known stabilized 3-isothiazolone dilute solutions suffer from having a high metal salt content so as to cause coagulation of latexes under certain conditions or from having limited stability. For example, U.S. Pat. No. 5,461,150 (Gironda, et al.), herein incorporated by reference, discloses the stabilization of dilute solutions of 5-chloro-2-methyl-3-isothiazolone, 2-methyl-3-isothiazolone and mixtures thereof with a low level of cupric ion in the form of a copper salt other than nitrate or nitrite. The weight ratio of the copper ion to the 3-isothiazolone compounds is in the range of 0.02:1.5 to 0.0008:1.5. These stabilized dilute solutions show good short term stability (4 weeks at 55° C., for example) but show no or limited long term stability (8 weeks at 55° C., for example). This patent does not address the problem of precipitate formation upon storage of the 3-isothiazolone compositions.

Although the use of stabilizers enables 3-isothiazolone dilute solutions to retain their microbicidal efficacy for a period of time, other problems may develop without significant loss of 3-isothiazolones, such as the formation of precipitate upon storage. The presence of this precipitate does not impact the efficacy of the 3-isothiazolones; however, the presence of the precipitate gives undesirable appearance to users of the product. It is clearly preferable from a commercial standpoint to have a product which does not form a precipitate.

Thus, there is a continuing need for 3-isothiazolone dilute solutions that have good long term stability and that are free of precipitate.

SUMMARY OF THE INVENTION

It has now been found that the addition of a small amount of an oxidant to a cupric ion stabilized 3-isothiazolone dilute solution greatly enhances the long term stability of the 3-isothiazolone while preventing precipitate formation upon storage.

The present invention provides a stable dilute solution composition of a microbicidal compound including: a) 0.5 to 5 wt % of a 3-isothiazolone compound selected from the group consisting of 5-chloro-2-methyl-3-isothiazolone, 2-methyl-3-isothiazolone, 5-chloro-2-ethyl-3-isothiazolone, 2-ethyl-3-isothiazolone, 4,5-dichloro-2-methyl-3-isothiazolone, and mixtures thereof; b) 2 to 500 ppm of cupric ion in the form of a copper salt; c) 0.01 to 10 wt % of an oxidant selected from the group consisting of chlorate salts, perchlorate salts, iodic acid, iodate salts, periodic acid, and periodate salts; and d) water; wherein the weight ratio of the cupric ion to the oxidant is 1:35 or greater.

The present invention further provides a method of preventing precipitate formation in a microbicide composition including the step of adding 0.01 to 10 wt %, based on the weight of the composition, of an oxidant selected from the group consisting of chlorate salts, perchlorate salts, iodic acid, iodate salts, periodic acid, and periodate salts to a stabilized 3-isothiazolone composition comprising 0.5 to 5 wt %, based on the weight of the composition, of a 3-isothiazolone compound selected from the group consisting of 5-chloro-2-methyl-3-isothiazolone, 2-methyl-3-isothiazolone, 5-chloro-2-ethyl-3-isothiazolone, 2-ethyl-3-isothiazolone, 4,5-dichloro-2-methyl-3-isothiazolone, and mixtures thereof; 2 to 500 ppm of a cupric ion in the form of a copper salt; and water; wherein the weight ratio of the cupric ion to the oxidant is 1:35 or greater.

The present invention is also directed to a method of controlling or inhibiting the growth of microorganisms in a locus including introducing to the locus a composition as described above.

DETAILED DESCRIPTION OF THE INVENTION

As used throughout the specification, the following terms shall have the following meanings, unless the context clearly indicates otherwise.

The term "microbicide" refers to a compound capable of inhibiting or controlling the growth of microorganisms at a locus. The term "microbicidal" refers to the activity of a compound to both eliminate and inhibit of the growth of microorganisms. The term "microorganism" includes, but is not limited to, fungi, bacteria, and algae. The term "locus" refers to an industrial system or product subject to contamination by microorganisms.

As used in this specification, the following abbreviations are applied: ppm =parts per million; g=gram; C=centigrade; UV=ultraviolet; HPLC=high performance liquid chromatography; mL=milliliter; DI=deionized; and wt %=percent by weight.

All percentages are by weight, based on the weight of the composition. All percentage by weight and ratio ranges are inclusive.

The 3-isothiazolones useful in the present invention are 5-chloro-2-methyl-3-isothiazolone, 2-methyl-3-isothiazolone, 5-chloro-2-ethyl-3-isothiazolone, 2-ethyl-3-isothiazolone, 4,5-dichloro-2-methyl-3-isothiazolone, and mixtures thereof. Preferred 3-isothiazolones are 5-chloro-2-methyl-3-isothiazolone, 2-methyl-3-isothiazolone, and mixtures thereof. Most preferred is a mixture of 5-chloro-2-methyl-3-isothiazolone and 2-methyl-3-isothiazolone. When in admixture, the preferred weight ratio of 5-chloro-2-methyl-3-isothiazolone to 2-methyl-3-isothiazolone is 90:10 to 2:98. Especially preferred is a weight ratio of 75:25 to 90:10.

The amount of the 3-isothiazolone compound in solution is 0.5 to 5.0 wt %, based on the weight of the composition. It is preferred to use 1 to 2 wt %, based on the weight of the composition.

A wide variety of copper salts are known in the art. Any copper salt which is sufficiently water soluble to provide the desired level of cupric ion in solution may be used. Suitable examples include, but are not limited to: copper sulfate, copper acetate, copper chloride, copper bromide, copper chlorate, copper perchlorate, copper nitrite and copper nitrate. Copper sulfate and copper nitrate are preferred. The copper salts are generally commercially available, for example, from Pfalz and Bauer (Waterbury, Conn.) and may be used without further purification.

The amount of cupric ion useful in the compositions of the present invention is typically 2 to 500 ppm. It is preferred to use 5 to 400 ppm, more preferably 30 to 200 ppm. Less cupric ion is needed at lower 3-isothiazolone concentrations than at higher concentrations. As the concentration of the isothiazolone is increased, proportionally more cupric ion is required to achieve the same stability. For example, 5 to 200 ppm of cupric ion is generally sufficient to stabilize a 1.5 wt % 3-isothiazolone dilute solution. It is preferred that the amount of cupric ion useful to stabilize a 1.5 wt % 3-isothiazolone dilute solution is 8 to 100 ppm. In general, 50 to 500 ppm of cupric ion is sufficient to stabilize 5 wt % 3-isothiazolone dilute solutions. It is preferred to use 150 to 500 ppm.

The oxidant useful in the present invention is selected from the group consisting of chlorate salts, perchlorate salts, iodic acid, iodate salts, periodic acid, and periodate salts. Suitable oxidants include, but are not limited to: sodium chlorate; potassium chlorate; sodium perchlorate; potassium perchlorate; iodic acid; lithium iodate; sodium iodate; potassium iodate; ammonium iodate; periodic acid; lithium periodate; sodium periodate; potassium periodate; and ammonium periodate. Preferred oxidants are sodium chlorate, potassium chlorate, sodium perchlorate, and potassium perchlorate. The oxidants are generally available from Aldrich Chemical Company (Milwaukee, Wis.) and may be used without further purification.

The amount of oxidant useful in the compositions of the present invention is 0.01 to 10 wt %, based on the weight of the composition. The amount of oxidant is preferably 0.05 to 8 wt %, and more preferably 0.1 to 5 wt %.

The weight ratio of cupric ion to oxidant useful in the compositions of the present invention is typically 1:35 or greater. The weight ratio of cupric ion to oxidant is preferably 1:35 to 1:300, and more preferably 1:50 to 1:200. Less oxidant is needed at lower cupric ion concentrations than at higher concentrations. As the concentration of the cupric ion is increased, proportionally more oxidant is required to achieve the same stability. For example, dilute solutions containing 1.5 wt % 3-isothiazolones and 8 to 200 ppm of cupric ion are generally stable and precipitate free if they contain 0.01 to 8 wt % of oxidant. Dilute solutions containing 5 wt % 3-isothiazolones and 50 to 500 ppm of a cupric ion are generally stable and precipitate free if they contain 0.5 to 10 wt % of oxidant, preferably 1 to 8 wt %.

Particularly useful compositions of the present invention comprise 1 to 2 wt %, based on the weight of the composition, of 2-methyl-3-isothiazolone, 5-chloro-2-methyl-3-isothiazolone or mixtures thereof; 5 to 100 ppm of cupric ion in the form of a copper salt; 0.05 to 8 wt % of an oxidant selected from the group consisting of sodium chlorate, potassium chlorate, sodium perchlorate, and potassium perchlorate; and water.

In preparing the compositions of the present invention, the oxidant cannot be added directly to the 3-isothiazolone. Otherwise, the 3-isothiazolone, copper salt, oxidant, and water can be mixed in any order. The compositions of the present invention are preferably prepared by mixing the 3-isothiazolone with water, followed by addition of the copper salt and then the oxidant.

The stabilized 3-isothiazolone dilute solutions of the present invention can be used to inhibit the growth of microorganisms by introducing a microbicidally effective amount of the composition onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; surfactants; industrial disinfectants or sanitizers, such as cold sterilants, hard surface disinfectants; floor polishes; laundry rinse water; fabric softeners; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; and pools and spas. Preferred loci are cosmetics and toiletries; latexes; emulsions and dispersions; paints; surfactants; floor polishes; fabric softeners; detergents; and household products.

The amount of 3-isothiazolone compounds suitable to inhibit or control the growth of microorganisms is well known in the art and depends upon the locus to be protected. The amount of 3-isothiazolone compounds suitable to inhibit the growth of microorganisms is generally between 0.05 and 5,000 ppm, based on the volume of said locus to be protected. It is preferred to use between 0.1 and 2,500 ppm. For example, loci such as a cooling tower or pulp and paper processing fluids require 0.1 to 100 ppm of the compounds of the present invention to inhibit microorganism growth. In cooling towers or pulp and paper processing fluids, it is preferred to use between 0.1 and 50 ppm. Other loci, such as construction products, oilfield fluids or emulsions, require 0.5 to 5000 ppm of the compounds of the present invention to inhibit microorganism growth, while loci such as disinfectants or sanitizers may require up to 5,000 ppm.

Because isothiazolones are so active as microbicides and only low levels of copper ion and halogen oxidant are required to achieve stabilization, the amount of copper ion and halogen oxidant in systems being treated will be very low. Therefore, the copper ion and halogen oxidant are not likely to interfere with other components in systems requiring protection or with other systems to which protected systems will be applied.

It is known in the art that the performance of microbicides may be enhanced by combination with one or more other microbicides. Thus, other known microbicides may be combined advantageously with the composition of this invention.

The following examples are presented to illustrate further various aspects of the present invention, but are not intended to limit the scope of the invention in any aspect. In the following examples, the 3-isothiazolones used were an approximate 3:1 mixture of 5-chloro-2-methyl-3-isothiazolone and 2-methyl-3-isothiazolone (96.5% pure). The level of copper is reported in ppm as the level of copper(II) ion. Samples were considered stable when no precipitate or phase separation occurred and greater than 85% of 5-chloro-2-methyl-3-isothiazolone remained after 8 weeks storage at 55° C. All samples were analyzed by HPLC with UV detection.

EXAMPLE 1

3-Isothiazolones from four different lots, A, B, C, and D, were used to prepare the following samples. To each of ten 100 mL glass bottles, labeled samples 1-1 to 1-10, were added 1.53 g of 3-isothiazolones from one of the lots. The specific lots used are shown in Table 1. To samples 1-1, 1-2, 1-3, and 1-4 were further added 0.0075 g of copper sulfate (30 ppm copper ion) and 98.5 g of DI water. To samples 1-5, 1-6, and 1-7 were added 0.025 g of copper sulfate (100 ppm copper ion) and 98.4 g of DI water. To samples 1-8, 1-9, and 1-10 were added 0.0503 g of copper sulfate (200 ppm cupric ion) and 98.4 g of DI water. All the samples contained 1.5 wt % 3-isothiazolones. The only stabilizer present in these samples was copper ion. The samples were capped, mixed to dissolve the salts, and stored in an oven at 55° C. The samples were analyzed for the percentage of 5-chloro-2-methyl-3-isothiazolone remaining after 4 and 8 weeks of storage. The results are reported below in Table 1.

TABLE 1

| Sample | 3-isothiazolone lot ID | Cupric Ion (ppm) | 4 Weeks | 8 Weeks | Precipitate* |
|---|---|---|---|---|---|
| 1-1 | A | 30 | 93 | 75 | + |
| 1-2 | B | 30 | 85 | 73 | + |
| 1-3 | C | 30 | 96 | 91 | + |
| 1-4 | D | 30 | 93 | 75 | + |
| 1-5 | A | 100 | 94 | 87 | + |
| 1-6 | B | 100 | 82 | 78 | + |
| 1-7 | D | 100 | 94 | 87 | + |
| 1-8 | A | 200 | 96 | 92 | + |
| 1-9 | B | 200 | 83 | 79 | + |
| 1-10 | D | 200 | 96 | 92 | + |

*"+" = precipitate present after 8 weeks storage

The above results show that while all the samples had good short term stability (4 weeks), long term stability was limited. The samples were visually inspected for the presence of precipitate after storage. A white precipitate was observed in all of the samples.

EXAMPLE 2

Four samples, labeled 2-1 to 2-4, were prepared according to Example 1. Samples 2-1 and 2-2 contained 30 ppm cupric ion; sample 2-3 contained 100 ppm copper ion; and sample 2-4 contained 200 ppm cupric ion. All samples contained 1.5 wt % of 3-isothiazolones. No other stabilizer was added to sample 2-1, which served as a control. To each of samples 2-2 to 2-4 was added 0.4 wt % sodium chlorate, based on the weight of the sample. The samples were capped, mixed, and then stored in an oven at 55° C. The samples were analyzed for the percentage of 5-chloro-2-methyl-3-isothiazolone remaining after 4 and 8 weeks of storage. The samples were also visually inspected for the presence of precipitate after 8 weeks of storage. The results are reported in Table 2.

TABLE 2

| Sample | Copper (ppm) | Sodium chlorate | 4 Weeks | 8 Weeks | Precipitate |
|---|---|---|---|---|---|
| 2-1 | 30 | — | 95 | 79 | +* |
| 2-2 | 30 | 0.4% | 97 | 97 | − |
| 2-3 | 100 | 0.4% | 99 | 99 | − |
| 2-4 | 200 | 0.4% | 99 | 99 | − |

*"+" = precipitate present; "−" = no precipitate present

These data clearly show that the addition of 0.4 wt % (400 ppm) of sodium chlorate to a cupric ion stabilized 3-isothiazolone dilute solution greatly increased the long term stability of the 3-isothiazolone at all levels of cupric ion and prevented the formation of undesirable precipitate.

EXAMPLE 3

This example demonstrates the stabilizing effect of cupric ion with periodic acid on 1.5 wt % isothiazolone dilute solutions. Three 1.5 wt % 3-isothiazolone dilute solutions, labeled 3-1, 3-2, and 3-3, were prepared according to Example 1. Samples 3-1 and 3-2 contained 30 ppm cupric ion. Sample 3-3 contained no cupric ion. To samples 3-2 and 3-3 was added 0.25 wt % periodic acid, based on the weight of the sample. The bottles were capped, mixed and stored in an oven at 55° C. The samples were analyzed for the percentage of 5-chloro-2-methyl-3-isothiazolone remaining after 4 and 8 weeks of storage. The samples were also visually inspected for the presence of a precipitate or the formation of a phase separated, orange layer. The results are reported in Table 3.

TABLE 3

| Sample | Copper | Periodic acid | 4 Weeks | 8 Weeks | 12 Weeks | Precipitate/ Phase separation |
|---|---|---|---|---|---|---|
| 3-1 | 30 ppm | — | 95 | 79 | 63 | +* |
| 3-2 | 30 ppm | 0.25% | 97 | 95 | 95 | − |
| 3-3 | — | 0.25% | 98 | 92 | 89 | ++ |

*"−" = no precipitate or phase separation; "+" = precipitate; "++" = phase separation (orange layer formed).

These data clearly show that the addition of 0.25 wt % (250 ppm) of periodic acid to a cupric ion stabilized 3-isothiazolone dilute solution greatly increased the long term stability of the 3-isothiazolone. The combination of cupric ion and periodic acid provided stable 3-isothiazolone dilute solutions that were also free of unwanted precipitate and phase separation.

EXAMPLE 4

Two 1.5 wt % 3-isothiazolone dilute solution samples, labeled 4-1 and 4-2, were prepared according to Example 1, using 3-isothiazolone lots A and B, respectively. Both samples 4-1 and 4-2 contained 100 ppm of cupric ion. To both samples was added 0.5 wt % sodium chlorate, based on the weight of the sample. The bottles were capped, mixed and stored in an oven at 55° C. The samples were analyzed for the percentage of 5-chloro-2-methyl-3-isothiazolone remaining after 4 and 8 weeks of storage. The results are reported in Table 4.

TABLE 4

| Sample | Cupric Ion (ppm) | Sodium Chlorate (wt %) | 3-Isothiazolone Lot | 4 Weeks | 8 Weeks |
| --- | --- | --- | --- | --- | --- |
| 4-1 | 100 | 0.5 | A | 98 | 97 |
| 4-2 | 100 | 0.5 | B | 98 | 94 |

These data clearly show that the compositions of the present invention have good long term stability.

EXAMPLE 5

Twelve 1.5 wt % 3-isothiazolone dilute solution samples, labeled 5-1 to 5-12, were prepared according to Example 1, using 3-isothiazolone lot D. Samples 5-1, 5-2, 5-5, 5-6, 5-9, and 5-10 contained 30 ppm cupric ion. Samples 5-3, 5-4, 5-7, 5-8, 5-11, and 5-12 contained 100 ppm cupric ion. To samples 5-1 to 5-4 was added 0.1 wt % sodium chlorate, based on the weight of the sample. To samples 5-5 to 5-8 was added 0.5 wt % sodium chlorate, based on the weight of the sample. To samples 5-9 to 5-12 were added 0.9 wt % sodium chlorate, based on the weight of the sample. The samples were capped, stored in an oven at 55° C., and analyzed after 8 weeks storage. The results are reported in Table 5.

TABLE 5

| Sample | Cupric Ion (ppm) | Sodium Chlorate (wt %) | Cupric Ion: Chlorate | 8 Weeks | Precipitate |
| --- | --- | --- | --- | --- | --- |
| 5-1 | 30 | 0.1 | 1:33 | 85 | +* |
| 5-2 | 30 | 0.1 | 1:33 | 77 | + |
| 5-3 | 100 | 0.1 | 1:10 | 84 | + |
| 5-4 | 100 | 0.1 | 1:10 | 86 | +/- |
| 5-5 | 30 | 0.5 | 1:167 | 89 | +/- |
| 5-6 | 30 | 0.5 | 1:167 | 86 | +/- |
| 5-7 | 100 | 0.5 | 1:50 | 94 | - |
| 5-8 | 100 | 0.5 | 1:50 | 90 | - |
| 5-9 | 30 | 0.9 | 1:300 | 97 | - |
| 5-10 | 30 | 0.9 | 1:300 | 96 | - |
| 5-11 | 100 | 0.9 | 1:90 | 100 | - |
| 5-12 | 100 | 0.9 | 1:90 | 93 | - |

*"+" = precipitate; "+/-" = some precipitate; "-" = no precipitate

The above data show that a cupric ion to oxidant weight ratio of 1:35 is necessary to provide stable 3-isothiazolone dilute solutions that are also precipitate free.

EXAMPLE 6 (Comparative)

This example shows that chlorate, without the addition of cupric ion, does not stabilize 3-isothiazolone dilute solutions. Six samples, labeled 6-1 to 6-6, were prepared according to Example 1, except that no copper sulfate was added. All samples contained 1.5 wt % 3-isothiazolones. To the samples was added sodium chlorate in either 0.1, 0.5 or 0.9 wt %, based on the weight of the sample. The samples were capped, stored in an oven at 55° C. and analyzed after 2 weeks storage for the percentage of 5-chloro-2-methyl-3-isothiazolone remaining. After 2 weeks storage, there was no 5-chloro-2-methyl-3-isothiazolone remaining in any of the samples. This clearly shows that chlorate alone is insufficient to stabilize 3-isothiazolone dilute solutions.

We claim:

1. A stable dilute solution composition of a microbicidal compound comprising:

a) 0.5 to 5 wt % of a 3-isothiazolone compound selected from the group consisting of 5-chloro-2-methyl-3-isothiazolone, 2-methyl-3-isothiazolone, 5-chloro-2-ethyl-3-isothiazolone, 2-ethyl-3-isothiazolone, 4,5-dichloro-2-methyl-3-isothiazolone, and mixtures thereof;

b) 2 to 500 ppm of cupric ion in the form of a copper salt;

c) 0.01 to 10 wt % of an oxidant selected from the group consisting of chlorate salts, perchlorate salts, iodic acid, iodate salts, periodic acid, and periodate salts; and d) water;

wherein the weight ratio of the cupric ion to the oxidant is 1:35 or greater.

2. The composition of claim 1 wherein the amount of the 3-isothiazolone compound is 1 to 2 wt %, based on the weight of the composition.

3. The composition of claim 1 wherein the copper salt is selected from the group consisting of: copper sulfate, copper acetate, copper chloride, copper bromide, copper chlorate, copper perchlorate, copper nitrite and copper nitrate.

4. The composition of claim 1 wherein the oxidant is selected from the group consisting of: sodium chlorate, potassium chlorate, sodium perchlorate, and potassium perchlorate.

5. The composition of claim 1 wherein the weight ratio of cupric ion to oxidant is 1:35 to 1:300.

6. A method of reducing precipitate formation in a microbicide composition comprising the step of adding 0.01 to 10 wt %, based on the weight of the composition, of an oxidant selected from the group consisting of chlorate salts, perchlorate salts, iodic acid, iodate salts, periodic acid, and periodate salts to a stabilized 3-isothiazolone composition comprising 0.5 to 5 wt %, based on the weight of the composition, of a 3-isothiazholone compound selected from the group consisting of 5-chloro-2-methyl-3-isothiazolone, 2-methyl-3-isothiazolone 5-chloro-2-ethyl-3-isothiazolone, 2-ethyl-3-isothiazolone, 4,5- dichloro-2-methyl-3-isothiazolone, and mixtures thereof; 2 to 500 ppm of a cupric ion in the form of a copper salt; and water; wherein the weight ratio of the cupric ion to the oxidant is 1:35 or greater, and wherein the composition is free of precipitate after 8 weeks of storage at 55° C.

7. The method of claim 6 wherein the copper salt is selected from the group consisting of copper sulfate, copper acetate, copper chloride, copper bromide, copper chlorate, copper perchlorate, copper nitrite and copper nitrate.

8. The method of claim 6 wherein the oxidant is selected from the group consisting of sodium chlorate, potassium chlorate, sodium perchlorate, and potassium perchlorate.

9. A method of controlling or inhibiting the growth of microorganisms in a locus comprising introducing to the locus the composition of claim 1.

10. The method of claim 9 wherein the locus is selected from the group consisting of: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; and metal working fluids.

* * * * *